(12) United States Patent
Heaton

(10) Patent No.: US 6,867,589 B2
(45) Date of Patent: Mar. 15, 2005

(54) METHOD FOR DETECTING HYDROCARBONS FROM NMR DATA

(75) Inventor: Nicholas J. Heaton, Houston, TX (US)

(73) Assignee: Schlumberger Technology Corporation, Sugar Land, TX (US)

(*) Notice: Subject to any disclaimer, the term of this patent is extended or adjusted under 35 U.S.C. 154(b) by 0 days.

(21) Appl. No.: 10/248,752

(22) Filed: Feb. 14, 2003

(65) Prior Publication Data
US 2004/0027123 A1 Feb. 12, 2004

Related U.S. Application Data

(60) Provisional application No. 60/319,460, filed on Aug. 9, 2002.

(51) Int. Cl.[7] .................................................. G01V 3/00
(52) U.S. Cl. ........................................ 324/303; 324/300
(58) Field of Search ................................. 324/303, 300, 324/307, 309, 311, 306, 318, 319

(56) References Cited

U.S. PATENT DOCUMENTS

| | | | |
|---|---|---|---|
| 5,680,043 A | 10/1997 | Hurlimann et al. ......... 324/303 |
| 5,696,448 A | 12/1997 | Coates et al. ............... 324/303 |
| 6,097,184 A | 8/2000 | Flaum ........................ 324/303 |
| 6,121,774 A * | 9/2000 | Sun et al. ................... 324/303 |
| 6,166,543 A * | 12/2000 | Sezginer et al. ............ 324/303 |
| 6,229,308 B1 | 5/2001 | Freedman ................... 324/303 |
| 6,232,778 B1 | 5/2001 | Speier et al. ............... 324/303 |
| 6,255,818 B1 | 7/2001 | Heaton et al. .............. 324/303 |
| 6,316,940 B1 * | 11/2001 | Akkurt ........................ 324/303 |
| 6,366,087 B1 | 4/2002 | Coates et al. ............... 324/303 |
| 6,400,147 B1 | 6/2002 | Toufaily et al. ............ 324/303 |
| 6,498,484 B1 * | 12/2002 | Sun et al. ................... 324/303 |
| 6,518,757 B1 | 2/2003 | Speier ........................ 324/303 |
| 6,522,136 B1 * | 2/2003 | Hurlimann et al. ......... 324/303 |
| 6,522,137 B1 | 2/2003 | Sun et al. ................... 324/303 |
| 6,522,138 B2 | 2/2003 | Heaton ....................... 324/303 |
| 6,534,980 B2 | 3/2003 | Toufaily et al. ............ 324/303 |
| 6,549,992 B1 | 4/2003 | Armangau et al. ......... 324/303 |
| 6,559,638 B1 | 5/2003 | Adelerhof ................... 324/303 |
| 6,570,382 B1 * | 5/2003 | Hurlimann et al. ......... 324/303 |
| 6,573,716 B2 | 6/2003 | Toufaily et al. ............ 324/303 |

OTHER PUBLICATIONS

Slijkerman, W.F.J. et al., Processing of Multi–Acquisition NMR Data, SPE 56768, Oct. 3–6, 1999 in Houston, Texas, pp. 641–647.

* cited by examiner

Primary Examiner—Brij B. Shrivastav
(74) Attorney, Agent, or Firm—Kevin P. McEnaney; Brigitte L. Echols

(57) ABSTRACT

A method for detecting hydrocarbons in a fluid sample includes deriving a difference measurement from a first nuclear magnetic resonance measurement and a second nuclear magnetic resonance measurement, wherein the first nuclear magnetic resonance measurement and the second nuclear magnetic resonance measurement have difference values in an acquisition parameter such that molecular diffusion affects the first nuclear magnetic resonance measurement and the second nuclear magnetic resonance measurement to a different extent; and determining a presence of hydrocarbons from the difference measurement.

28 Claims, 6 Drawing Sheets

METHOD FOR DETECTING HYDROCARBONS FROM NMR DATA

CROSS REFERENCE TO RELATED APPLICATIONS

This application claims priority to U.S. Provisional Application No. 60/319,460 filed Aug. 9, 2002, by Nicholas Heaton, entitled Method for Detecting Hydrocarbons from NMR Data.

BACKGROUND OF INVENTION

1. Field of the Invention

The present invention relates to the field of well logging. More specifically, the present invention relates to methods for detecting hydrocarbons in reservoirs using nuclear magnetic resonance data.

2. Background Art

Oil and gas exploration and production are very expensive operations. Any knowledge about the formations that can help reduce the unnecessary waste of resources in well drilling is invaluable. Because of this, the oil and gas industry has developed various tools capable of determining and predicting earth formation properties. Among different types of tools, nuclear magnetic resonance (NMR) instruments have been successfully used in a wide variety of applications. NMR instruments can be used to determine formation properties, such as the fractional volume of pore space and the fractional volume of mobile fluid filling the pore space. A general background of NMR well logging is described in U.S. Pat. No. 6,140,817.

Nuclear magnetic resonance is a phenomenon occurring in a selected group of nuclei having magnetic nuclear moments, i.e., non-zero spin quantum numbers. $^1$H (proton) is the species commonly detected in NMR well logging because of its natural abundance and sensitivity to NMR measurements. When these nuclei are placed in a magnetic field ($B_o$, "Zeeman field"), they each precess around the axis of the $B_o$ field with a specific frequency, the Larmor frequency ($\omega_o$), which is a characteristic property of each nuclear species (gyromagnetic ratio, $\gamma$) and depends on the magnetic field strength ($B_o$) effective at the location of the nucleus, i.e., $\omega_o = \gamma B_o$.

Both water and hydrocarbons in earth formations produce detectable NMR signals. It is desirable that the signals from water and hydrocarbons be separable so that hydrocarbon-bearing zones may be identified. However, it is not always easy to distinguish which signals are from water and which are from hydrocarbons. Various methods have been proposed to separately identify water and hydrocarbon signals.

The differential spectrum (DSM) and shifted spectrum (SSM) methods proposed by Akkurt et. al. in "NMR Logging of Natural Gas Reservoirs" Paper N. Transactions of the Society of Professional Well Log Analysts (SPWLA) Annual Logging Symposium, 1995, compare $T_2$ distributions derived from two Carr-Purcell-Meiboom-Gill (CPMG) measurements performed with different polarization times (DSM) or echo-spacings (SSM). A modification to these methods, known as time domain analysis (TDA), was later introduced by Prammer et al. in "Lithology-Independent Gas Detection by Gradient-NMR Logging," SPE paper 30562, 1995. In TDA, "difference" data are computed directly in the time domain by subtracting one set of data measured amplitudes from the other. The difference dataset is then assumed to contain only light oil and/or gas. In TDA, relative contributions from light oil or gas are derived by performing a linear least squares analysis of the difference data using assumed NMR responses for these fluids. Both DSM and TDA assume that the water signal has substantially shorter $T_1$ relaxation times than those of the hydrocarbons. This assumption is not always valid, however. Most notably, this assumption fails in formations where there are large pores or where the hydrocarbon is of intermediate or high viscosity. The SSM method and its successor, the enhanced diffusion method (EDM) proposed by Akkurt et. al. in "Enhanced Diffusion: Expanding the Range of NMR Direct Hydrocarbon Typing Applications", Paper GG. Transactions of the Society of Professional Well Log Analysts (SPWLA) Annual Logging Symposium, 1998, separate gas, oil and water contributions based on changes in the $T_2$ distributions that result from changes in the echo spacing of CPMG measurements. The methods are applicable in a limited range of circumstances and the accuracy of the result is significantly compromised by incomplete separation of water and hydrocarbon signals in the $T_2$ domain. Moreover, these methods are designed to function with CPMG sequences. However, with the diffusion-based methods, CPMG pulse sequences provide poor signal to noise ratios due to the reduced number of echoes that can be measured. A strategy for combining and selecting these different NMR methods has been described recently by Coates et al. in U.S. Pat. No. 6,366,087 B1.

The second approach to NMR hydrocarbon detection is more generally applicable. These methods typically apply forward modeling to suites of NMR data acquired with different parameters. The suite of NMR data are typically acquired with different echo spacings (TE) or polarization times (WT), and sometimes acquired with different magnetic field gradients (G). There are currently two methods in this approach: the MACNMR proposed by Slijkerman et al., SPE paper 56768, "Processing of Multi-Acquisition NMR Data", 1999, and the Magnetic Resonance Fluid characterization (MRF) method disclosed in U.S. Pat. No. 6,229,308 B1 issued to Freedman and assigned to the assignee of the present invention ("the Freedman patent"). The Freedman patent is hereby incorporated by reference.

The MRF method is capable of obtaining separate oil and water $T_2$ distributions. This method uses a Constituent Viscosity Model (CVM), which relates relaxation time and diffusion rates to constituent viscosities whose geometric mean is identical to the macroscopic fluid viscosity. With the MRF method, estimates for water and hydrocarbon volumes are obtained by applying a forward model to simulate the NMR responses to a suite of NMR measurements acquired with different parameters. In addition to fluid volumes, the MRF method also provides estimates of oil viscosity. The MRF method represents the most comprehensive and accurate method currently available for NMR fluid characterization in well-logging. Unlike the above-mentioned methods, the MRF method is applicable to any suite of NMR measurements and is not limited to the CPMG sequences. In fact, it has been successfully applied to NMR measurements acquired with diffusion-editing (DE) sequences.

While the prior art methods are useful in predicting the presence of hydrocarbons in the formations, it is desirable to have simpler methods that can predict the presence of hydrocarbons in the formations from NMR data and are generally applicable to NMR data acquired with different pulse sequences.

SUMMARY OF INVENTION

One aspect of the invention relates to methods of predicting the presence of hydrocarbons in a fluid sample. The fluid sample may be connate fluids in an earth formation, a formation fluid sample removed with a formation tester, and other fluids. A method for detecting hydrocarbons in a fluid sample includes deriving a difference measurement from a first nuclear magnetic resonance measurement and a second nuclear magnetic resonance measurement, wherein the first nuclear magnetic resonance measurement and the second nuclear magnetic resonance measurement have difference values in an acquisition parameter such that molecular diffusion affects the first nuclear magnetic resonance measurement and the second nuclear magnetic resonance measurement to a different extent; and determining a presence of hydrocarbons from the difference measurement.

Another aspect of the invention relates to methods of well logging. A method for nuclear magnetic resonance logging of a formation penetrated by a wellbore includes acquiring a first nuclear magnetic resonance measurement; acquiring a second nuclear magnetic resonance measurements, wherein the first nuclear magnetic resonance measurement and the second nuclear magnetic resonance measurement have different values in an acquisition parameter so that molecular diffusion affects the first nuclear magnetic resonance measurement and the second nuclear magnetic resonance measurement to a different extent; and determining a difference measurement from the first nuclear magnetic resonance measurement and the second nuclear magnetic resonance measure.

Other aspects and advantages of the invention will be apparent from the following description and the appended claims.

DETAILED DESCRIPTION

The invention relates to methods for filtering out water signals in NMR measurements of formation fluids. Embodiments of the invention are generally applicable to common NMR data, irrespective of pulse sequences used in NMR data acquisition. According to one method of the invention, NMR data from two (or more) measurements (e.g., DE measurements) are combined such that the resulting combined dataset contains signal amplitudes from hydrocarbon only. In effect the method filters out water signals and yields oil signals which can subsequently be interpreted with the aid of a suitable fluid model (e.g., CVM) to provide estimates for oil saturation and viscosity. In the following description, methods of the invention will be illustrated using NMR measurements acquired using DE pulse sequences. One skilled in the art would appreciate that it could equally be adapted to a broad range of other NMR measurement schemes including standard CPMGs. The NMR measurements acquired with DE pulse sequences are referred to as "DE measurements" in this description.

The diffusion-editing (DE) pulse sequence is introduced by Hürlimann et al. See M. D. Hürlimann et al., "*Diffusion-Editing: New NMR Measurement of Saturation and Pore Geometry,*" paper presented at the 2002 Annual Meeting of the Society of Professional Well Log Analysts, Osio, Japan, June 2–5; see also, U.S. application Ser. No. 09/723,803 filed on Nov. 28, 2000 by Hürlimann, entitled "*Simpler and More Robust Hydrocarbon Typing with Pulsed NMR.*" This application is assigned to the same assignee as the present invention and is hereby incorporated by reference.

Figure 1:
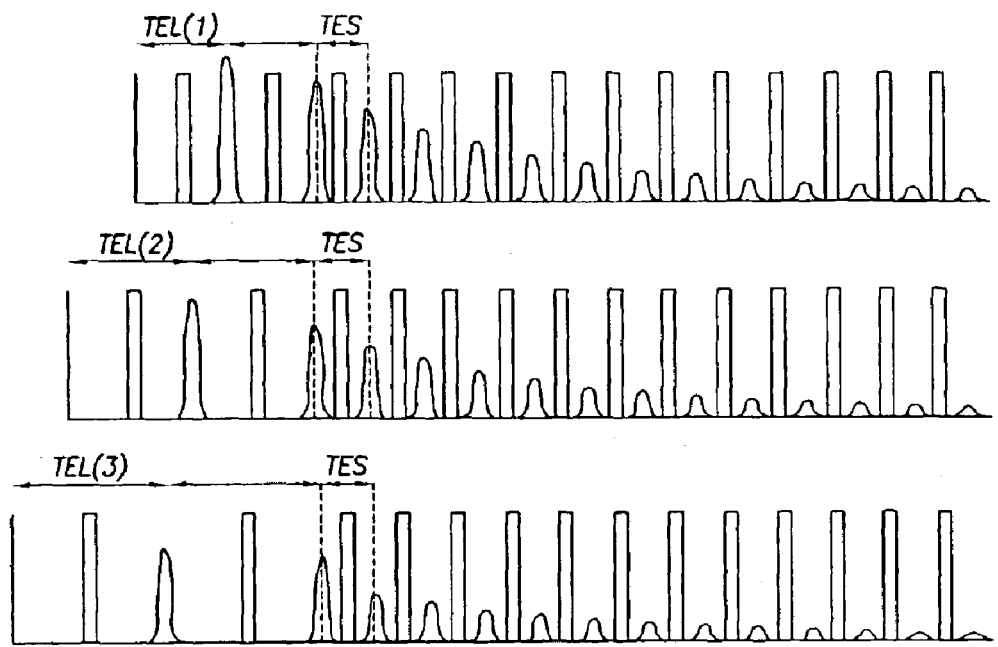
FIG. 1 shows three DE pulse sequences with different long inter-echo delay times.

DE pulse sequences are similar to the CPMG sequences except that the initial two echoes are acquired with longer echo spacings and the third and subsequent echoes are acquired with shorter echo spacings. FIG. 1 shows three DE pulse sequences with different long echo spacings (TEL) for the first two echoes. The third and subsequent echoes have echo spacings (TES) that are as short as possible. In DE pulse sequences shown in FIG. 1, diffusion information is encoded during the acquisition of the first two echoes, whereas the third and subsequent echoes provide bulk and surface relaxation time information with relatively little attenuation of the signal by diffusion. Although the DE pulse sequences shown in FIG. 1 have two echoes with long echo spacings, one skilled in the art would appreciate that other numbers (e.g., 1, 3, 4, etc.) of such echoes may be used without departing from the scope of the invention. Using a conventional CPMG sequence to encode the diffusion information requires a long inter-echo spacing, which results in poor bulk and surface relaxation time information because diffusion decay attenuates the signal after relatively few echoes. Consequently, a suite of data acquired with DE sequences provides better diffusion information and signal-to-noise ratio in the spin-echo data, as compared to an analogous suite acquired with CPMG sequences. Therefore, DE sequences can provide more accurate and robust computations of brine and oil $T_2$ distributions than CPMG sequences.

The echo amplitude, M, from a diffusion editing (DE) measurement of a sample containing oil and water can be expressed as $$M(t, WT, TEL, TES) = F(t, WT)Z(t, TEL, TES) + M_O(t, WT, TEL, TES) \quad (1)$$

where t is the time of the echo after the initial 90° excitation pulse, TEL is the long echo spacing, TES is the short echo spacing, and WT is the effective wait time of the measurement. The first term on the right of Equation (1), $F(t,WT)Z(t,TEL,TES)$, represents the water contribution to the signal. The function $F(t,WT)$ accounts for attenuation of the water signal due to transverse and longitudinal relaxation. Attenuation of the water signal due to diffusion is described by $Z(t, TEL, TES)$. In general, oil signal attenuation cannot be separated into diffusion and intrinsic relaxation terms. However, for the following description, it is not necessary to separate these terms. Thus, the contribution of oils to the overall echo amplitude is simply denoted as $M_O$ (t, WT, TEL, TES) in this description.

For water, the first attenuation term, $F(t,WT)$, can be written explicitly in terms of the $T_2$ distribution, $A(T_2)$, $$F(t, WT) \int A(T_2)(1 - e^{-WT/T_1(T_1)})e^{-t/T_2} dT_2 \quad (2)$$

and the diffusion term is given by:

$$Z(t, TEL, TES) = \delta_{TEL,TES} e^{-R_{1,S}2} + (1 - \delta_{TEL,TES})e^{-R_{1,S}(t-2TEL)} \quad (3)$$

$$[\alpha e^{-2R_{1,L}TEL} + \beta e^{-4R_{1,L}TEL}]$$

where $\alpha$ and $\beta$ are attenuation coefficients for the direct and stimulated echoes and are known constants for a particular tool. The water diffusion relaxation rates for short and long echo spacings are:

$$R_{2S} = \frac{D_W(\gamma \cdot G \cdot TES)^2}{12}, \quad R_{2L} = \frac{D_W(\gamma \cdot G \cdot TEL)^2}{12} \quad (4)$$

where $D_W$ is the water diffusion constant, $\gamma$ is the proton gyromagnetic ratio, and G is the magnetic field gradient.

Equation (4) shows that if the water diffusion constant ($D_W$) can be estimated with a reasonable accuracy, then the water diffusion rates ($R_{2,S}$ and $R_{2,L}$) as shown in Equation (4) can be calculated. With the water diffusion rates, $R_{2,S}$ and $R_{2,L}$, known, the diffusion term, Z(t,TEL,TES), in Equation (3) can be computed. Accordingly, the echo amplitude M(t,WT,TEL,TES) shown in equation (1) can be re-written as a modified echo amplitude, in which the water diffusion effect during the first two (long) echoes is removed entirely. This modified echo amplitude may be defined as:

$$M^*(t, WT, TEL, TES) = \frac{M(t, WT, TEL, TES)}{Z(T, TEL, TES)} \quad (5)$$

$$= F(t, WT)e^{-R_{1,S}(t-T)} +$$

$$\frac{M_o(t, WT, TEL, TES)}{Z(T, TEL, TES)}$$

where T is an arbitrary reference time chosen to be equal to or longer than twice the longest TEL value in the measurement suite, i.e., $T \leq 2*TEL$. Note that the first term on the right of the equation, $F(t,WT)\exp(-R_{2,S}(t-T))$, represents the water contribution to the modified echo decays and is independent of the long echo spacing, TEL. Therefore, this water contribution term can be removed completely by taking the difference of two modified decays, M*(t,WT,TEL,TES), with different TEL values, TEL(1) <TEL(2). If we set T=2*TEL(2), the difference signal, after rescaling by Z(t,TEL(2),TES), is:

$$S(t, WT, TEL(1), TEL(2), TES) = Z(T, WT, TEL(2), TES) \times \quad (6)$$

$$= (M^*(t, WT, TEL(2), TES) -$$

$$M^*(t, WT, TEL(1), TES))$$

$$= M_o(t, WT, TEL(2), TES) -$$

$$\frac{Z(T, WT, TEL(2), TES)}{Z(T, WT, TEL(1), TES)}$$

$$M_o(t, WT, TEL(1), TES)$$

Equation (6) states that the difference decay, S(t,WT,TEL (1),TEL(2),TES), includes signal magnitudes only from oil, while the only remnant of water contribution appears as a ratio of the two diffusion terms, i.e., the ratio of the Z functions in Equation (6). Because the remnant of water contribution only appears as a ratio of the Z functions, any error in estimating the water diffusion constant ($D_W$) will be partially cancelled and will not significantly influence the accuracy of the difference decay, S(t,WT,TEL (1), TEL(2), TES), shown in Equation (6). Similarly, the validity of a free diffusion model for water presumed in Equation (4) will not have a significant impact on the accuracy of the difference decay, S (t,WT,TEL(1),TEL(2),TES), shown in Equation (6). Furthermore, because the ratio of the Z functions can be made very small by selecting TEL(2)>>TEL(1), the second term in Equation (6) disappears and the difference decay can be made approximately equal to the oil signals for the TEL(2) measurement, $$S(t,WT,TEL(1), TEL(2) \approx M_o(t,WT,TEL(2),TES) \quad (7)$$

In effect, methods of the invention can filter out water signals from individual diffusion-editing echoes at t>T. The only requirement for using methods of the invention is that two DE measurements with different long echo spacings (TEL) are acquired. The accuracy of methods of the invention depends only on the validity of the free-diffusion model and the accuracy of the estimated water diffusion constant ($D_W$). The method provides a direct measure of the oil/water diffusion contrast and minimizes errors that can arise from incorrect selection of fluid parameters, particularly in low contrast environments. Note that the description above has assumed that the hydrocarbon is oil, which typically diffuses more slowly than water. However, the method may equally be applied to gas reservoirs. In this case, the gas diffuses more rapidly than water and the resultant difference signal may have a negative amplitude that is proportional to the gas volume.

Although the above description assumes that two DE measurements are separately acquired and then one is subtracted from the other, one skilled in the art would appreciate that the subtraction may alternatively be performed during data acquisition. For example, an NMR logging tool may be programmed to perform the following steps: (1) a first DE measurements with TEL(2) is acquired, (2) the first DE measurement is stored in the memory, (3) a second DE measurement with TEL(1) is acquired, and (4) second DE measurement is subtracted from the first DE measurement. The subtraction may be achieved by multiplying the second DE measurement with a constant 1 and adding the resultant data to the memory. Alternatively, the second DE measurement may be acquired by shifting the phase of the excitation pulse by 180°. The resultant second DE measurement can then be directly added to the first DE measurement.

Although the above description uses different TEL values to illustrate the methods of the invention, one skilled in the art would appreciate that the same results may be obtained by varying the magnetic field gradients.

Figure 2:
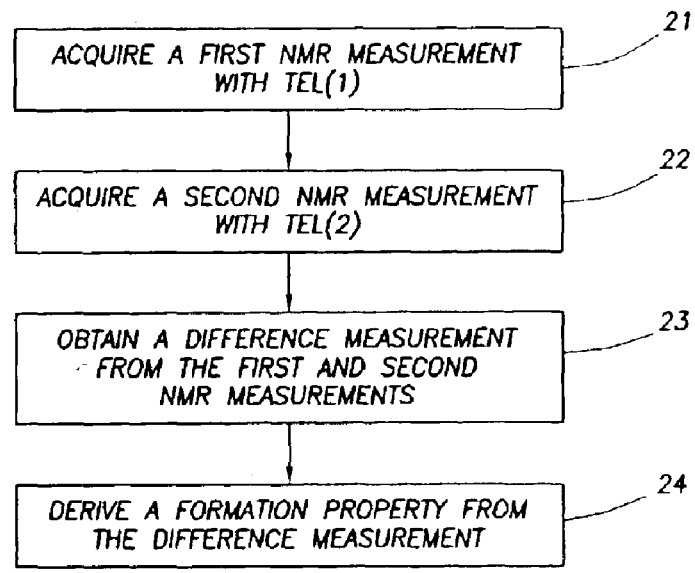
FIG. 2 shows a flow chart of a method according to one embodiment of the invention.

FIG. 2 illustrates one method according to embodiments of the invention. First, an NMR measurement is acquired, for example using a DE pulse sequence and a long echo spacing TEL(1) (shown as 21). Then, a second NMR measurement is acquired with the same parameters except for the long echo spacing, TEL(2) (shown as 22). The NMR measurements are shown to be acquired with DE pulse sequences. However, other pulse sequences (e.g., CPMG sequences) may also be used. The two NMR measurements are then subtracted one from the other to produce a difference measurement (shown as 23). As stated above, this difference measurement may also be obtained during acquisition, rather than post acquisition. That is, steps 21–23 may be accomplished in a single step.

The difference measurement thus obtained can then be analyzed with any suitable methods to provide formation properties (shown as 24). For example, the difference measurement may be inverted to provide $T_2$ distributions of the oils. Alternatively, it may be analyzed with the MRF method to provide $T_2$ distributions of individual oil components, e.g., gas, light oil, and heavy oil. The $T_2$ distributions can then be used to derive formation properties, such as fluid volumes, viscosities, and porosities. Note that if one wishes to derive formation porosities from the difference measurements, it would be necessary to adjust the amplitudes of the difference measurements or the resultant porosities by a water diffusion scaling factor.

Figures 3, 4:
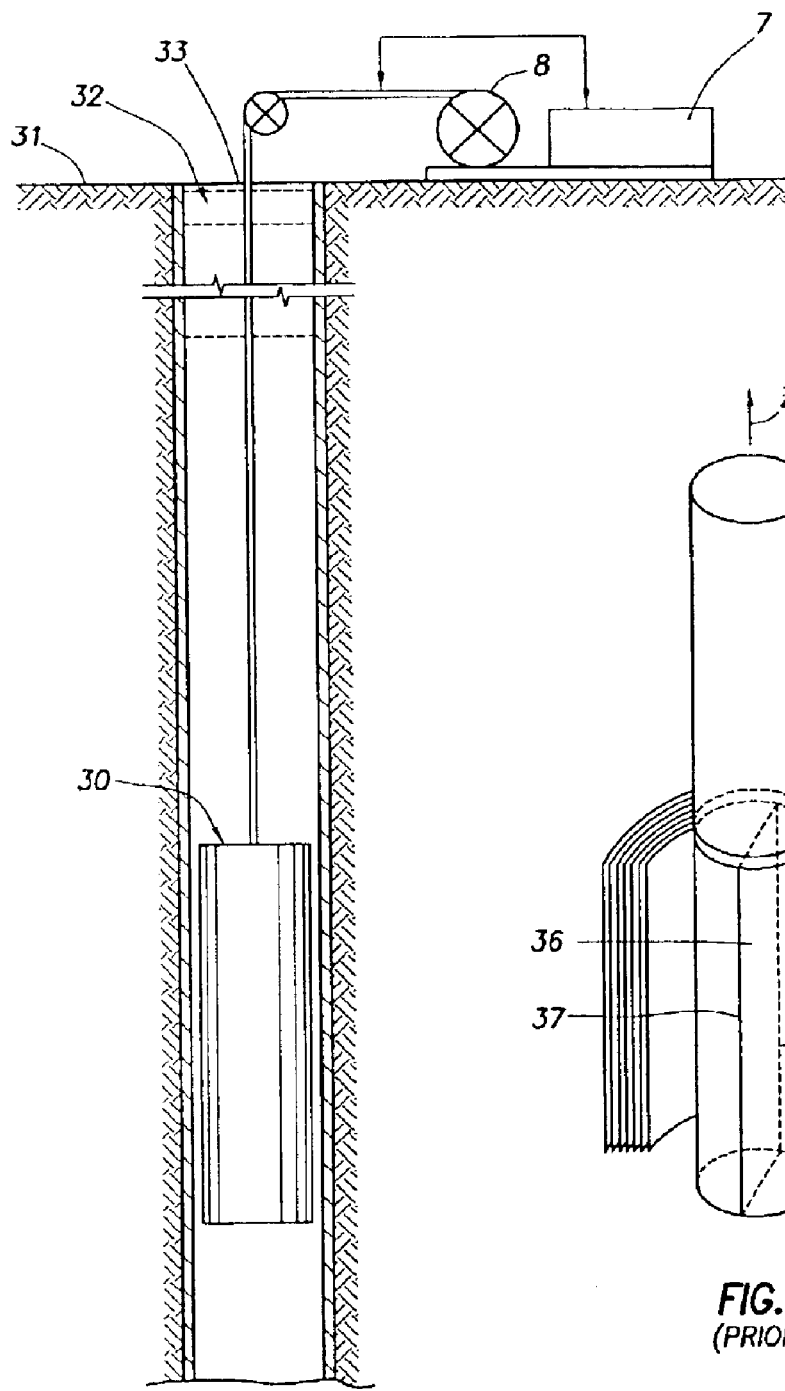
FIG. 3 shows a prior art NMR well logging system.
FIG. 4 shows components of a prior art NMR instrument.

Acquisition of NMR-measurements according to embodiments of the invention may be accomplished with various methods of NMR measurements known in the art. For example, the measurements may be performed in a laboratory using a sample removed from an earth formation. Alternatively, the NMR measurements may be performed in a logging operation using a wireline tool, a logging-while-drilling or measurement-while-drilling tool, or a formation tester. FIG. 3 illustrates a schematic of an NMR logging system. In FIG. 3, a nuclear magnetic resonance (NMR) logging tool 30 for investigating earth formations 31 traversed by a borehole 32 is shown. The NMR logging device 30 is suspended in the borehole 32 on an armored cable 33, the length of which substantially determines the relative axial depth of the device 30. The cable length is controlled by suitable means at the surface such as a drum and winch mechanism 8. Surface equipment 7 can be of conventional type and can include a processor subsystem which communicates with downhole equipment including NMR logging device 30.

The NMR logging device 30 can be any suitable nuclear magnetic resonance logging device; it may be one for use in wireline logging applications as shown in FIG. 3, or one that can be used in logging-while-drilling (LWD) or measurement-while-drilling (MWD) applications. In addition, the NMR logging device 30 may be part of any formation tester known in the art, such as that sold under the trade name of MDT™ by Schlumberger Technology Corporation (Houston, Tex.). The NMR logging device 30 typically includes a means for producing a static magnetic field in the formations, and a radio frequency (RF) antenna means for producing pulses of magnetic field in the formations and for receiving the spin echoes from the formations. The means for producing a static magnetic field may comprise a permanent magnet or magnet array, and the RF antenna means for producing pulses of magnetic field and receiving spin echoes from the formations may comprise one or more RF antennas.

FIG. 4 illustrates a schematic of some of the components of one type of NMR logging device 30. FIG. 4 shows a first centralized magnet or magnet array 36 and an RF antenna 37, which may be a suitably oriented coil or coils. FIG. 4 also illustrates a general representation of closely-spaced cylindrical thin shells, 38-1, 38-2 . . . 38-N, that can be frequency selected in a multi-frequency logging operation. One such device is disclosed in U.S. Pat. No. 4,710,713. In FIG. 4, another magnet or magnet array 39 is shown. Magnet array 39 may be used to pre-polarize the earth formation ahead of the investigation region as the logging device 30 is raised in the borehole in the direction of arrow Z. Examples of such devices are disclosed in U.S. Pat. Nos. 5,055,788 and 3,597,681.

Figure 5:
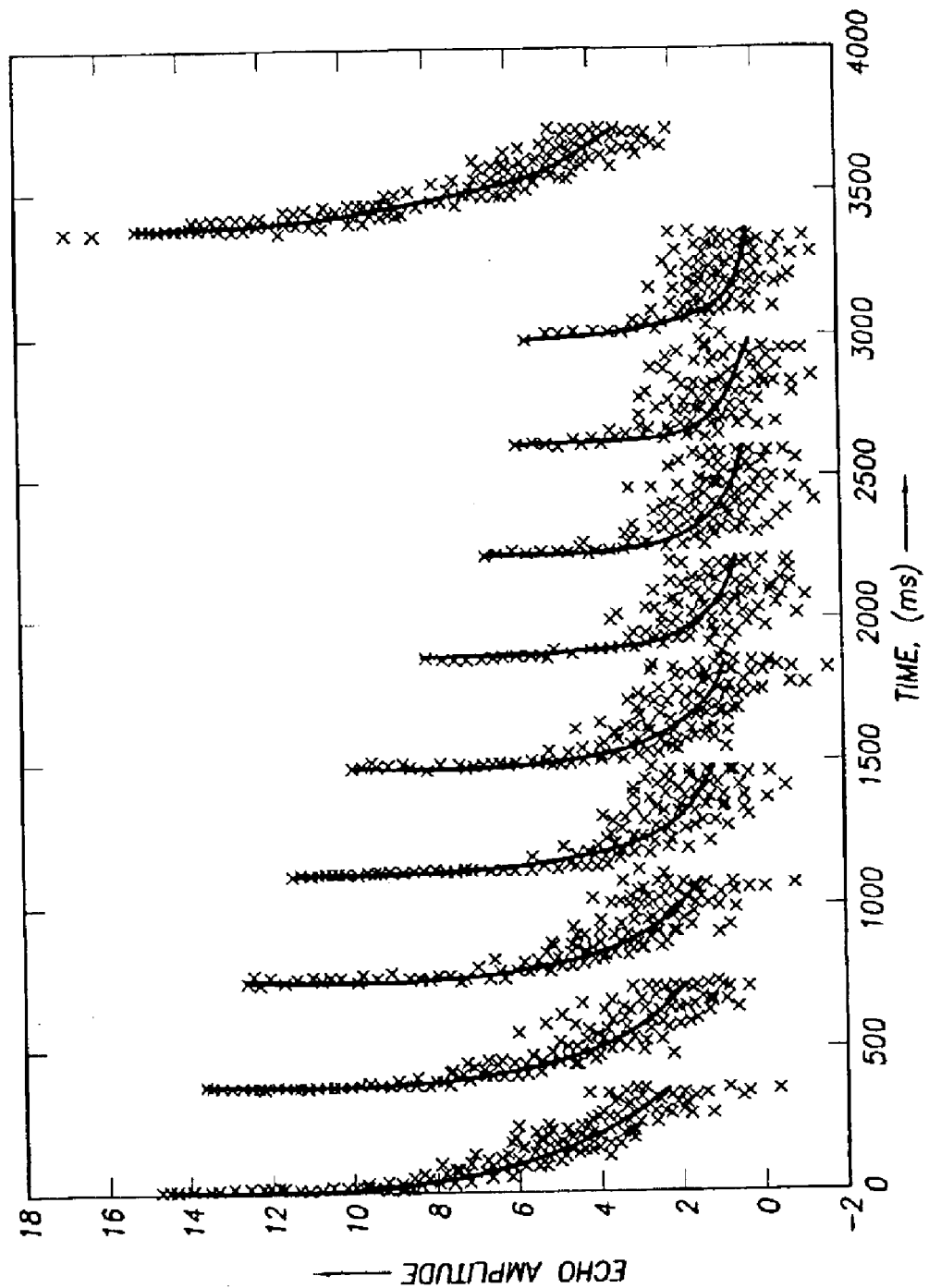
FIG. 5 shows NMR measurements obtained with DE and CPMG pulse sequences.

Embodiments of the invention will now be illustrated with the following examples. In the first example, a method according to the invention is applied to downhole data acquired in a field test of an oil field in Indiana. A suite of nine DE measurements was acquired with long echo spacings (TEL) of 2, 4, 5, 6, 7, 8.5, 10, 11, 12 ms, followed by a standard CPMG. Each measurement used the same long wait time (WT) and 600 echoes were acquired with a short echo spacing of 0.6 ms. FIG. 5 shows the nine DE measurements as well as the standard CPMG measurement. The standard CPMG measurement is equivalent to a DE measurement with the first two echoes having the same inter-delay (TEL=0.6 ms) as that of the remainder of the echoes (TES=0.6 ms), i.e., TEL=TES. The solid curves in FIG. 5 represent post-inversion fit of these data using the MRF method.

Figure 6A:
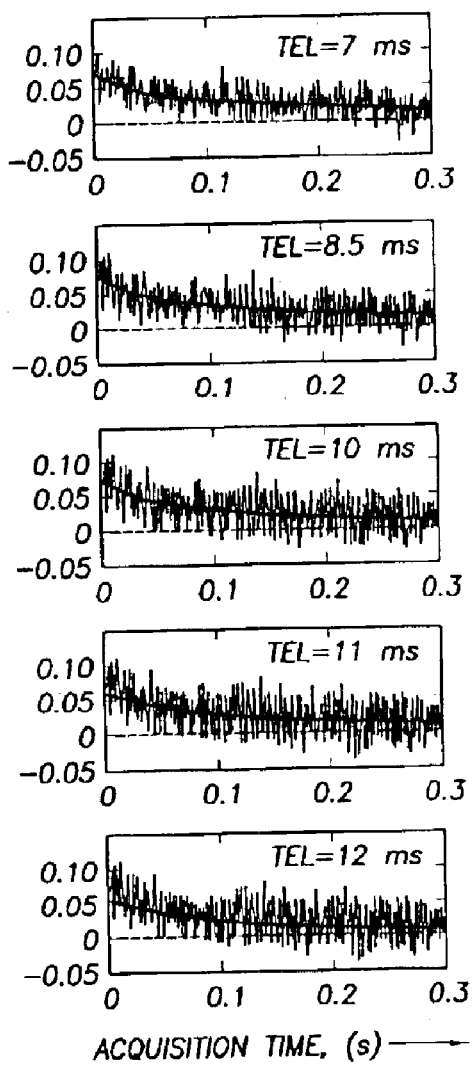
FIG. 6A shows oil-only measurements obtained with a method of the invention.

FIG. 6A shows 5 difference measurements resulted from subtracting the CPMG measurement from the last 5 DE measurements according to Equations (5) and (6). These difference measurements include "oil-only" decays because the water decays have been filtered out by methods of the invention.

FIG. 6A clearly shows that the modified decays are consistent with the presence of oil because the decay amplitudes are non-zero.

Figure 6B:
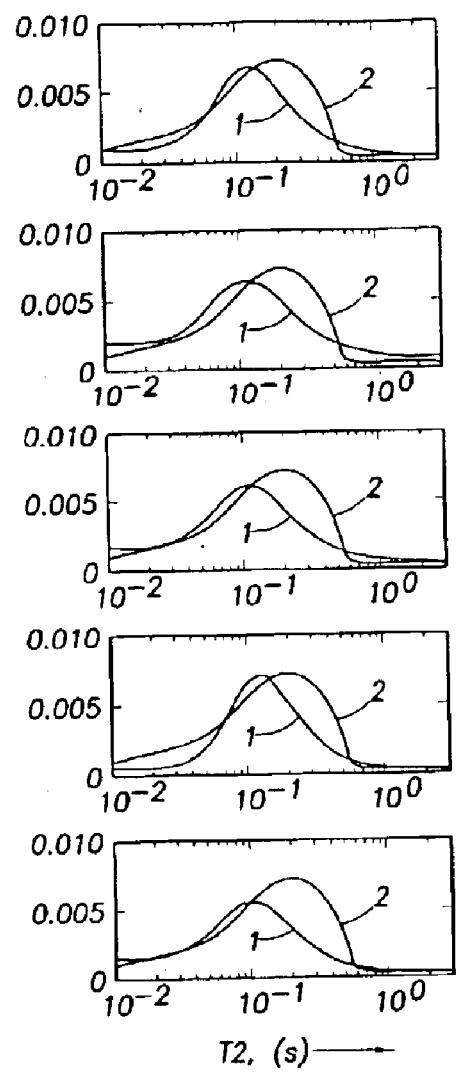
FIG. 6B shows the corresponding $T_2$ distributions derived from the oil-only measurements.

The corresponding $T_2$ distributions derived from these 5 "oil-only" measurements are shown in FIG. 6B (curve 1). For comparison, FIG. 6B also includes the $T_2$ distributions measured for the produced oil sample (curve 2). As shown in FIG. 6B, the $T_2$ distributions computed from the data set generated with a method of the invention (curve 1) are in reasonable agreement with the $T_2$ distributions measured for a produced oil sample (curve 2). FIG. 6B also shows that the estimated $T_2$ distributions computed by methods of the invention have an apparent loss of intensity in the long $T_2$ components (above 100 ms). This loss of long $T_2$ components is due in part to regularization effects, but primarily reflects the reduced relative contribution of the long $T_2$ components to the modified decay signals.

As shown in FIG. 6B, the estimated oil $T_2$ distributions are relatively insensitive to the value of TEL, over the range of TEL values used here. The $T_2$ distributions shown in FIG. 6B may be further analyzed to provide estimates for formation properties such as oil volumes and viscosities. Table 1 shows results from such an analysis.

TABLE 1

Oil volumes, Log Mean $T_2$ and Viscosity Derived from "Oil-Only" Echo Decays

| TEL (ms) | Oil Volume (p.u.) | $T_{2LM}$ (ms) | Viscosity (cp) |
|---|---|---|---|
| 7 | 3.5 | 130 | 10 |
| 8.5 | 3.9 | 110 | 11 |
| 10 | 3.6 | 110 | 12 |
| 11 | 3.1 | 130 | 9 |
| 12 | 3.1 | 100 | 13 |

Data are from the 5 difference DE measurements of the Indiana field test as shown in FIGS. 6A and 6B. Values shown are not corrected for attenuation of the oil signals.

It should be noted that the quantities reported in Table 1 have not been corrected for attenuation of the oil signals due to relaxation, diffusion, or signal loss associated with the change of echo spacings in the DE measurements. These values also take no account of the data manipulation used to derive the oil-only echo decays. That is, these values have not been adjusted for attenuations that might result from the derivation of the oil-only decays. The attenuation of the oil signals is included in Equation (6). In order to compute the magnitudes of the attenuation, it is necessary to use some model for the oil relaxation and diffusion properties. The Constituent Viscosity Model (CVM) provides a suitable model for this purpose. One skilled in the art would appreciate that other suitable models may also be used.

Figure 7:
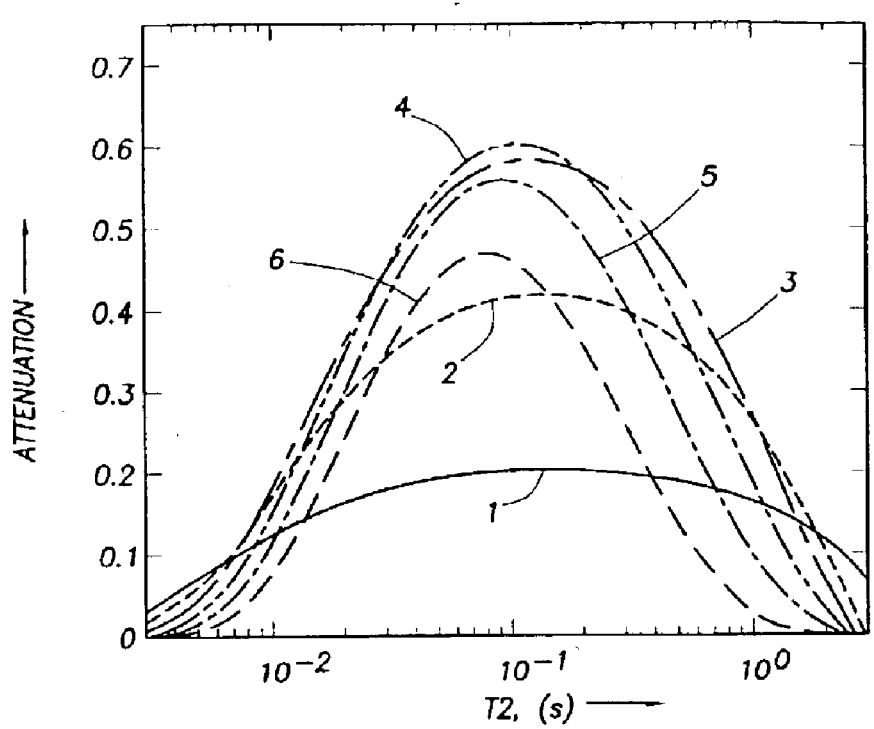
FIG. 7 shows attenuation functions with respect to various long inter-echo delay times in a DE pulse sequence.

FIG. 7 shows the sensitivity functions (i.e. attenuation) of the oil contribution as a function of $T_2$. Oil signal attenuations are computed using the CVM model and the same tool parameters ($\alpha$, $\beta$) used previously for the derivation of the oil decays. In FIG. 7, curves 1–7 represent the attenuation functions for TEL=3, 5, 7, 8.5, 10, and 12 ms, respectively. These attenuation functions reflect the contribution of an oil component with a particular $T_2$ value to the modified decay. The results shown in FIG. 7 were computed using a field gradient of 34 G/cm.

FIG. 7 shows that the attenuations are dependent on $T_2$ and are greatest for long $T_2$ components. This is consistent with the increased diffusion rate of the lighter oil components and hence reduced oil/water contrast. The $T_2$ distribution of the oil sample (shown as curve 2 in FIG. 6B) exhibits significant amplitude up to 400 ms, indicating that the attenuation factor could be significant in the computed "oil-only" decays.

In principal, the attenuation profiles may be used to boost the long $T_2$ components in the measured oil $T_2$ distributions, in much the same way as the polarization correction is applied to account for incomplete polarization in standard NMR logging. However, such an approach is not recommended because the compensation factors for the long $T_2$ components could be significant and would be subject to the vagaries of regularization and any other inversion artifacts. Thus, in the preferred embodiments of the invention, this correction is not applied. Visual inspection of the attenuation profiles in FIG. 7 and the oil $T_2$ distributions in FIG. 6B suggests that the initial uncorrected oil volumes should be boosted by approximately a factor of 2. This would lead to oil saturation estimates of about 0.4 0.5, in reasonable agreement with the MRF estimates (0.4 0.5) for the same data.

Figure 8:
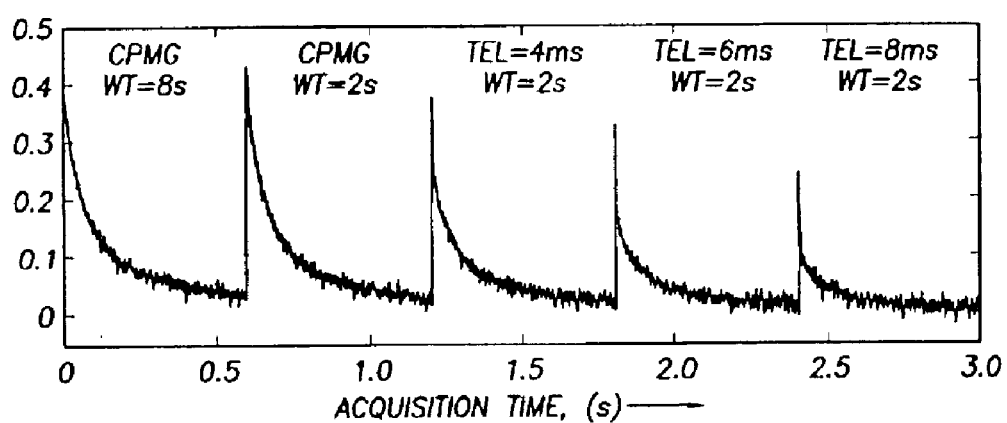
FIG. 8 shows five measurements from a water well.

Methods of the invention have also been applied to DE data acquired in a water well. The data used for this analysis correspond to cumulative averages of a DE depth log from a water well. The averaged data are shown in FIG. 8. In FIG. 8, the first two measurements are acquired with CPMG pulse sequences having WT=8 s and 2 s, respectively, and the last three measurements are acquired with DE pulse sequences, each with WT=2 s, but with different TEL as shown (4 ms, 6 ms, and 8 ms). These measurements were acquired with a magnetic field gradient of 23 G/cm.

For the analysis, only the last 4 measurements (i.e., the second CPMG and the 3 DE measurements) are used. As before, the CPMG measurement is used as the "reference" measurement (i.e. TEL(1) measurement). The resulting "oil-only" decays are presented in FIG. 9 (curve 1), together with the corresponding raw DE data (curve 2), plotted on the same scale for comparison. Clearly the "oil-only" decays (curve 1) appear as noise on the baseline, indicating the absence of oil. This is as expected because this is a water well. Computed oil volumes are practically within the noise level.

Figure 9:
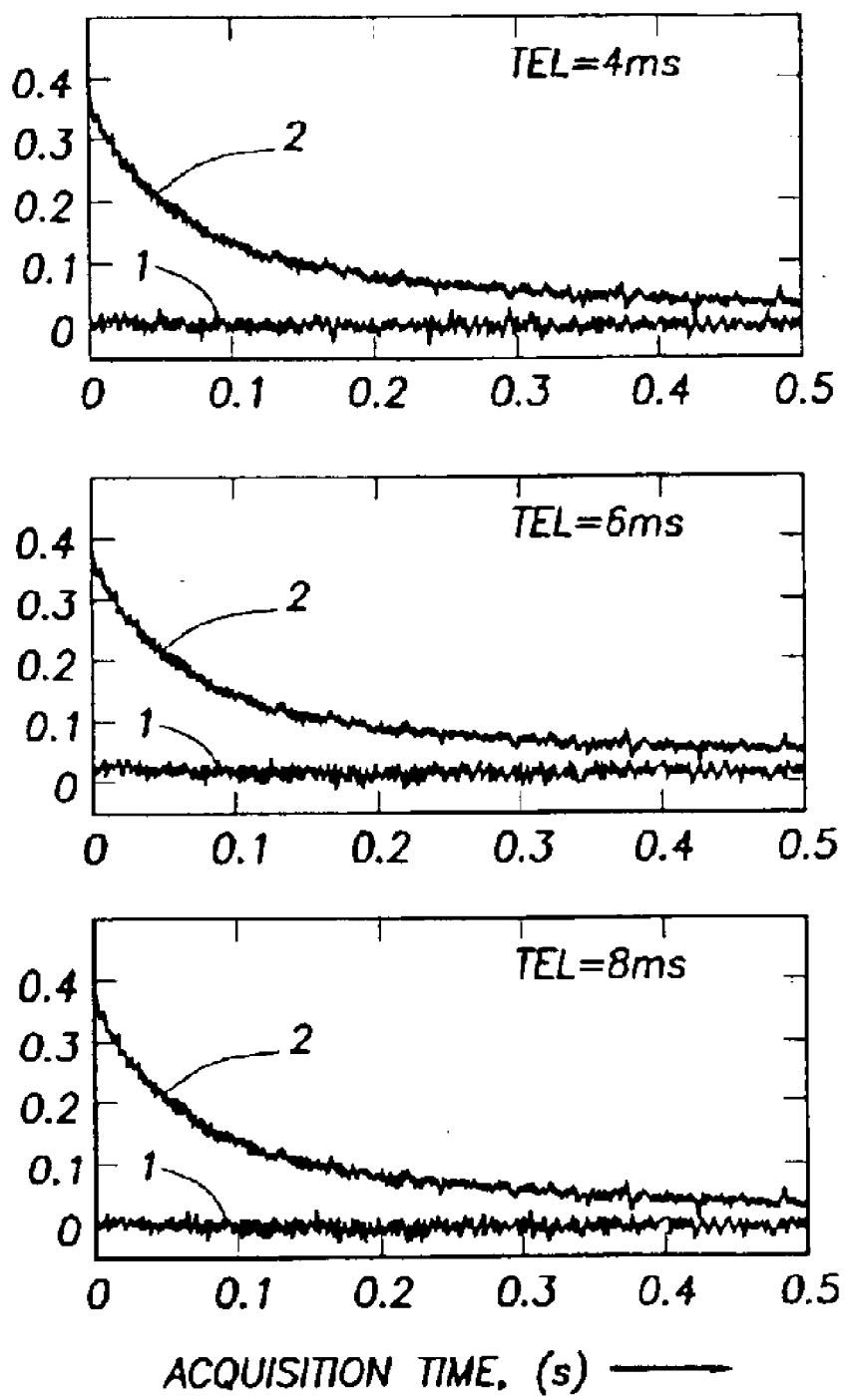
FIG. 9 shows the oil-only measurements as calculated from the measurements shown in FIG. 8. The corresponding DE measurements are also shown for reference.

The results shown in FIG. 9 demonstrate that methods of the invention work when oil is not present, as well as when oil is present.

Once the oil is identified, the "oil-only" measurement (echo train) may be inverted to provide the oil $T_2$ distributions. Alternatively, saturation and viscosity estimates can be computed by inverting the "oil-only" echo train and invoking a model (e.g., CVM) to account for oil signal attenuation. The resultant oil signal can be viewed as the measured NMR contrast or used as a quantitative confidence indicator for other comprehensive analysis (e.g., MRF) of the data. In addition, the fluid viscosity and saturations derived with methods of the invention may be compared with the same values derived with other methods as a cross-check for fluid property estimates.

Methods of the invention have the following advantages. Embodiments of the invention provide simple linear methods to effectively filter out water signals from NMR measurement data, leaving a set of echoes corresponding to oil-only signals. In effect, methods of the invention separate the identification of oil from subsequent steps of characterization. The identification step requires no prior knowledge or model for the oil NMR properties. As stated earlier, precise knowledge of the water diffusion constant and the validity of free diffusion model have less impact on the accuracy of methods of the invention.

Unlike prior art "difference" methods (e.g., DSM, SSM), methods of the invention can provide difference measurement substantially without water contribution. The methods require only 2 measurements (although more may be used) with different long echo spacing (or field gradient) values. Within reasonable limits, results are relatively insensitive to the precise choice of measurement parameters, as shown in FIGS. 6A and 6B.

Although the method has been demonstrated for diffusion editing measurements in which the first two echoes have different echo-spacings from subsequent echoes, the approach could be generalized to other NMR measurement sequences. The method could be used with measurements acquired with the same or different field gradients. The method can also be applied to tools with distributions of field gradients, such as the CMR™ tool from Schlumberger Technology Corporation (Houston, Tex.).

While the invention has been described with respect to a limited number of embodiments, those skilled in the art, having the benefit of this disclosure, will appreciate that other embodiments can be devised which do not depart from the scope of the invention as disclosed herein. For example, embodiments of the invention may be practiced with a wireline tool as well as a LWD or MWD tool. In addition, embodiments of the invention may be practiced on a fluid sample removed by a formation tester and the NMR measurements are either acquired in the formation tester or in a laboratory. Accordingly, the scope of the invention should be limited only by the attached claims.

What is claimed is:

1. A method for detecting hydrocarbons in a fluid sample, comprising:

acquiring a first nuclear magnetic resonance measurement and a second nuclear magnetic resonance measurement, wherein the first nuclear magnetic resonance measurement and the second nuclear magnetic resonance measurement are acquired with different values in an acquisition parameter such that molecular diffusion affects differently the first nuclear magnetic resonance measurement and the second nuclear magnetic resonance measurement;

deriving a difference measurement from the first and the second nuclear magnetic resonance measurements after scaling at least one of the first and the second nuclear magnetic resonance measurements with a factor derived from a water diffusion constant; and determining a presence of hydrocarbons from the difference measurement.

2. The method of claim 1, wherein the first nuclear magnetic resonance measurement and the second nuclear magnetic resonance measurement are acquired with a diffusion-editing pulse sequence.

3. The method of claim 2, wherein the first nuclear magnetic resonance measurement and the second nuclear magnetic resonance measurement are acquired with different long echo spacings.

4. The method of claim 3, wherein the deriving the difference measurement comprises converting the first nuclear magnetic resonance measurement into a first modified nuclear magnetic resonance measurement and converting the second nuclear magnetic resonance measurement into a second modified nuclear magnetic resonance measurement, the first and second modified nuclear magnetic resonance measurements being substantially free of contributions from water diffusion during the long echo spacings.

5. The method of claim 4, wherein the difference measurement comprises a difference between the first modified nuclear magnetic resonance measurement and the second modified nuclear magnetic resonance measurement.

6. The method of claim 5, wherein the difference measurement is substantially free of contributions from water relaxations.

7. The method of claim 1, wherein the first nuclear magnetic resonance measurement and the second nuclear magnetic resonance measurement are acquired with different magnetic field gradients.

8. The method of claim 1, wherein the first nuclear magnetic resonance measurement and the second nuclear magnetic resonance measurement are acquired with a Carr-Purcell-Meiboom-Gill pulse sequence.

9. The method of claim 1, wherein the deriving the difference measurement is performed during data acquisition.

10. The method of claim 1, wherein the fluid sample comprises formation fluids removed by a formation tester.

11. The method of claim 1, wherein the fluid sample is in one selected from the group consisting of an earth formation and a core sample removed from an earth formation.

12. The method of claim 11, further comprising deriving a formation property from the difference measurement.

13. The method of claim 12, wherein the deriving comprises obtaining transverse relaxation time distributions from the difference measurement.

14. The method of claim 12, wherein the formation property comprises one selected from fluid viscosity, fluid saturation, and apparent porosity.

15. The method of claim 1, wherein the determining comprises estimating an apparent hydrocarbon filled porosity from a magnitude of the difference measurement.

16. The method of claim 1, wherein the determining comprises deriving transverse relaxation time distributions from the difference measurement.

17. The method of claim 1, wherein the determining comprises deriving transverse relaxation time distributions for individual hydrocarbon components from the difference measurement using a magnetic resonance fluid characterization method.

18. The method of claim 17, wherein the individual hydrocarbon components comprise gas, light oil, and heavy oil.

19. The method of claim 1, wherein the hydrocarbons comprise at least one selected from the group consisting of oil and gas.

20. A method for nuclear magnetic resonance logging of a formation penetrated by a wellbore, comprising:
disposing a nuclear magnetic resonance logging tool in the wellbore;
acquiring a first nuclear magnetic resonance measurement;
acquiring a second nuclear magnetic resonance measurements, wherein the first nuclear magnetic resonance measurement and the second nuclear magnetic resonance measurement are acquired with different values in an acquisition parameter such that molecular diffusion affects the first nuclear magnetic resonance measurement and the second nuclear magnetic resonance measurement;
deriving a difference measurement from the first and the second nuclear magnetic resonance measurement after scaling at least one of the first and the second nuclear magnetic resonance measurements with a factor derived from a water diffusion constant; and
determining a presence of hydrocarbons from the difference measurement.

21. The method of claim 20, wherein the acquiring the first nuclear magnetic resonance measurement and the acquiring the second nuclear magnetic resonance measurement are performed with a diffusion-editing pulse sequence.

22. The method of claim 21, wherein the first nuclear magnetic resonance measurement and the second nuclear magnetic resonance measurement are acquired with different long echo spacings.

23. The method of claim 22, wherein the determining the difference measurement comprises deriving a first modified nuclear magnetic resonance measurement from the first nuclear magnetic resonance measurement and deriving a second modified nuclear magnetic resonance measurement from the second nuclear magnetic resonance measurement.

24. The method of claim 23, wherein the first modified nuclear magnetic resonance measurement and the second nuclear magnetic resonance measurement are substantially free of contributions from water diffusion during the long echo spacings.

25. The method of claim 24, wherein the difference measurement comprises a difference between the first modified nuclear magnetic resonance measurement and the second modified nuclear magnetic resonance measurement.

26. The method of claim 25, wherein the difference measurement is substantially free of contributions from water relaxation.

27. The method of claim 20, wherein the first nuclear magnetic resonance measurement and the second nuclear magnetic resonance measurement are acquired with different magnetic field gradients.

28. The method of claim 20, wherein the acquiring the first nuclear magnetic resonance measurement and the acquiring the second nuclear magnetic resonance measurement are performed with a Carr-Purcell-Meiboom-Gill pulse sequence.

* * * * *